(12) United States Patent
Holmqvist

(10) Patent No.: US 11,766,522 B2
(45) Date of Patent: Sep. 26, 2023

(54) ACTIVATION ASSEMBLY FOR A MEDICAMENT DELIVERY DEVICE

(71) Applicant: SHL MEDICAL AG, Zug (CH)

(72) Inventor: Anders Holmqvist, Värmdö (SE)

(73) Assignee: SHL MEDICAL AG, Zug (CH)

( * ) Notice: Subject to any disclaimer, the term of this patent is extended or adjusted under 35 U.S.C. 154(b) by 232 days.

(21) Appl. No.: 17/330,814

(22) Filed: May 26, 2021

(65) Prior Publication Data

US 2021/0275755 A1    Sep. 9, 2021

Related U.S. Application Data

(63) Continuation of application No. 16/348,848, filed as application No. PCT/EP2017/080189 on Nov. 23, 2017, now Pat. No. 11,202,867.

(30) Foreign Application Priority Data

Nov. 29, 2016   (EP) .................................... 16201284

(51) Int. Cl.
    *A61M 5/32*    (2006.01)
    *A61M 5/20*    (2006.01)
    *A61F 9/00*    (2006.01)
    *A61M 5/315*    (2006.01)

(52) U.S. Cl.
CPC ........ *A61M 5/3202* (2013.01); *A61M 5/2033* (2013.01); *A61M 5/3243* (2013.01);
(Continued)

(58) Field of Classification Search
CPC .............. A61M 5/3202; A61M 5/2033; A61M 5/3243; A61M 2005/2013;
(Continued)

(56) References Cited

U.S. PATENT DOCUMENTS

| 9,744,302 B2 | 8/2017 | Travanty |
| 2017/0319793 A1 | 11/2017 | Bergens |
| 2019/0001060 A1* | 1/2019 | Gylleby ............ A61M 5/31568 |

FOREIGN PATENT DOCUMENTS

| CN | 104667387 A | 6/2015 |
| CN | 104780962 A | 7/2015 |

(Continued)

OTHER PUBLICATIONS

International Search Report and Written Opinion for Int. App. No. PCT/EP2017/080189, dated Jan. 31, 2018.
(Continued)

*Primary Examiner* — James D Ponton
*Assistant Examiner* — Neeraja Gollamudi
(74) *Attorney, Agent, or Firm* — MCDONNELL BOEHNEN HULBERT & BERGHOFF LLP

(57) ABSTRACT

An activation assembly for a medicament delivery device is presented having a delivery member cover provided with legs and configured to be biased in a proximal direction, a movable sleeve configured to be received between the legs, and an activation sleeve configured to be biased in the proximal direction, wherein the delivery member cover is configured to be moved in an axial direction between a first position and a second position, wherein movement of the delivery member cover from the first position to the second position causes movement of the movable sleeve from a first movable sleeve position to a second movable sleeve position. The delivery member cover axially displaces the activation sleeve in a distal direction when the delivery member cover moves towards the second position, thereby causing a first actuation of a sensor. The activation sleeve is configured to move in the proximal direction when the delivery member cover returns from the second position to the first position, thereby providing a second actuation of the sensor.

20 Claims, 7 Drawing Sheets

(52) U.S. Cl.
CPC .......... *A61F 9/0008* (2013.01); *A61M 5/3157* (2013.01); *A61M 2005/2013* (2013.01); *A61M 2205/276* (2013.01); *A61M 2205/581* (2013.01); *A61M 2205/8206* (2013.01)

(58) Field of Classification Search
CPC .... A61M 2205/276; A61M 2205/8206; A61M 2005/2073; A61M 2005/208; A61M 2005/3247; A61M 5/20; A61M 5/31501; A61M 5/326; A61M 5/31535
See application file for complete search history.

(56) References Cited

FOREIGN PATENT DOCUMENTS

| | | |
|---|---|---|
| CN | 106029133 A | 10/2016 |
| TW | 201244770 A | 11/2012 |
| TW | 201542259 A | 11/2015 |
| TW | I592184 B | 7/2017 |
| TW | I598122 B | 9/2017 |
| TW | I604866 B | 11/2017 |
| WO | 2007/107564 A1 | 9/2007 |
| WO | 2015/187797 A1 | 12/2015 |
| WO | 2016/034407 A2 | 3/2016 |
| WO | 2016/055305 A1 | 4/2016 |
| WO | 2016/078863 A1 | 5/2016 |
| WO | 2016/091554 A1 | 6/2016 |
| WO | 2016/120207 A1 | 8/2016 |
| WO | 2016/128207 A1 | 8/2016 |

OTHER PUBLICATIONS

Chinese Office Action for CN Application No. 201780070018.0, dated Dec. 31, 2020.

\* cited by examiner

ACTIVATION ASSEMBLY FOR A MEDICAMENT DELIVERY DEVICE

CROSS REFERENCE TO RELATED APPLICATIONS

The present application is a continuation of U.S. patent application Ser. No. 16/348,848, filed May 9, 2019, which is a U.S. National Phase Application pursuant to 35 U.S.C. § 371 of International Application No. PCT/EP2017/080189 filed Nov. 23, 2017, which claims priority to European Patent Application No. 16201284.3 filed Nov. 29, 2016. The entire disclosure contents of these applications are herewith incorporated by reference into the present application.

TECHNICAL FIELD

The present disclosure generally relates to medicament delivery devices. In particular, it relates to an activation assembly for a medicament delivery device.

BACKGROUND

Modern medicament delivery devices, such as auto-injectors, are designed to facilitate medicament administration in a manner which allows users to administer medicaments themselves. This freedom for patients to handle medicament delivery has lead to the concept of adherence, or compliance, to become an increasingly important area in treatment of illnesses. Adherence involves monitoring of a patient's medication administration scheme as prescribed by a physician and evaluation of whether a prescribed medicament and medicament administration scheme has been successful or not in treating the illness of the patient.

It has been found that it is relatively common that a user does not administer the medication as prescribed. Reasons for a patient's failure to comply with the prescribed scheme include forgetfulness, pain associated with drug administration or discomfort experienced from side effects of the medication.

Failure to comply with a drug administration scheme may result in that the patient can experience poor recovery from an illness, and it may furthermore result in secondary diseases requiring additional medical attention. This may in turn bring unnecessary pressure on the healthcare system.

In view of the above, it is in the interest of both patients' and the healthcare to facilitate monitoring to increase the occurrences of medicament administration as prescribed.

WO2007/107564 A1 discloses an electronic module for mechanical medication delivery devices, and aims at monitoring the operation of a medication delivery device. This document discloses an electronic module that is attached onto a medication delivery device. The electronic module is capable of measuring acoustical and/or vibrational signals generated in response to relative movements of internal parts of the medication delivery device to which the electronic module is attached. Such internal parts can be mechanical parts which during movement generate for example acoustical sounds, such as click sounds. The electronic module is powered by a built-in battery which powers the module when for example a capacitive touch pad is activated. This activation is performed when for example a fingertip is positioned on the touch pad.

In WO2007/107564 A1 the battery and thus the electronic module is activated provided a user touches the touch pad located on the electronic module. This touch pad is not associated with the mechanical operation of the medication delivery device. There is hence a risk that a user will forget to activate the electronic module prior to drug administration. This would result in that the following drug administration would not be registered.

SUMMARY

An object of the present disclosure is to provide an activation assembly for a medicament delivery device which solves or at least mitigates problems of the prior art.

There is hence according to a first aspect of the present disclosure provided an activation assembly for a medicament delivery device, wherein the activation assembly comprises: a delivery member cover provided with legs and configured to be biased in a proximal direction, a movable sleeve configured to be received between the legs, and an activation sleeve configured to be biased in the proximal direction, wherein the delivery member cover is configured to be moved in an axial direction between a first position relative to the movable sleeve and a second position relative to the movable sleeve, wherein movement of the delivery member cover from the first position to the second position causes movement of the movable sleeve from a first movable sleeve position to a second movable sleeve position, wherein the delivery member cover is configured to axially displace the activation sleeve in a distal direction when the delivery member cover is moved towards the second position, the activation sleeve being configured to thereby provide a first actuation of a sensor of an electronics assembly of the medicament delivery device, wherein the activation sleeve is configured to move in the proximal direction when the delivery member cover returns from the second position to the first position, thereby providing a second actuation of the sensor, and wherein the movable sleeve is configured to prevent the delivery member cover from moving from the first position to the second position when the delivery member cover has returned from the second position to the first position.

The activation sleeve is hence configured, upon distal movement of the delivery member cover, to provide a first actuation of a sensor of an electronics assembly of a medicament delivery device. This actuation of the sensor may for example provide a registration of the commencement of a medicament administration by the electronics assembly. It furthermore ensures that the sensor is actuated whenever the delivery member cover is moved distally, which is during a medicament administration procedure, so that compared to WO2007/107564 A1, it may be made certain that registration of a medicament administration can always be obtained. Additionally, the subsequent proximal movement of the delivery member cover and thus of the activation sleeve causes the second actuation of the sensor, whereby it may be registered by the electronics assembly that the medicament delivery procedure is being completed.

The activation sleeve may be configured to constantly contact the sensor while the delivery member cover is in the second position, so that the second actuation of the sensor occurs when the activation sleeve is released from or ceases being in contact with the sensor.

According to one embodiment the movable sleeve is rotatable relative to the delivery member cover, and movement of the delivery member cover from the first position to the second position causes rotation of the movable sleeve, wherein the first movable sleeve position is a first rotational position and the second movable sleeve position is a second rotational position.

According to one embodiment the delivery member cover has a distal end surface configured to cooperate with a radially extending portion of the movable sleeve, forming a cam surface, wherein cooperation between the distal end surface and the radially extending surface causes the rotation of the movable sleeve.

According to one embodiment the movable sleeve has a tangentially extending radially flexible first tongue configured to allow the delivery member cover to move over the first tongue towards the second position when the movable sleeve is in the first rotational position and to prevent the delivery member cover to move from the first position to the second position when the movable sleeve is in the second rotational position and the delivery member cover has returned to the first position.

According to one embodiment the first tongue has an increasing thickness in the tangential direction, whereby the first tongue is configured to enable the delivery member cover to move over the first tongue, in the axial direction, from the first position towards the second position, when the movable sleeve is in the first rotational position.

According to one embodiment the movable sleeve has a radially outwards extending protrusion configured to cooperate with the delivery member cover to prevent rotation of the movable sleeve from the second rotational position to the first rotational position.

According to one embodiment the movable sleeve has a tangentially extending radially flexible second tongue, wherein the radially outwards extending protrusion is provided on the second tongue.

One embodiment comprises an electronics assembly including an energy storage unit and processing circuitry configured to register activation of a medicament administration procedure.

According to one embodiment the electronics assembly comprises a sensor in the form of a switch, and the activation sleeve is configured to provide the first actuation of the switch.

According to one embodiment the switch extends radially outwards and is radially flexible, wherein the activation sleeve is configured to provide the first actuation of the switch by moving distally, over the switch, thereby pressing the switch radially inwards and to provide the second actuation of the switch by moving proximally, away from the switch, thereby releasing the switch from being pressed radially inwards.

According to one embodiment the movable sleeve is configured to be arranged proximally relative to the activation sleeve.

According to one embodiment the activation sleeve has proximally extending arms configured to be axially aligned with and to cooperate with a respective leg of the delivery member cover, the delivery member cover thereby pushing the activation sleeve when moved from the first position to the second position causing the axial displacement of the activation sleeve.

According to one embodiment activation sleeve has a distally extending arm configured to actuate the sensor.

There is according to a second aspect of the present disclosure provided a medicament delivery device comprising: a housing, and an activation assembly according to the first aspect, configured to be received by the housing.

The medicament delivery device also includes the electronics assembly, either arranged inside the housing, or included in a supplementary device, i.e. an add-on device, configured to be mounted to the main body of the medicament delivery device.

One embodiment comprises a plunger rod configured to move axially inside the housing from an initial position to an end position, and an end click member configured to be released and thrown in the distal direction when the plunger rod has travelled a majority of the distance from the initial position to the end position, and an end click sensor configured to detect impact of the end click member upon being released, causing the electronics assembly to register completion of medicament expulsion.

In this manner, three different actuations/detections may be registered by the electronics assembly, namely the first and second actuation of the sensor, and also the detection of impact of the end click member. It may thereby be possible to determine, by means of the electronics assembly, commencement of medicament administration based on the first actuation, completion of, or almost completion of, medicament administration by means of detecting impact of the end click member, and determining that e.g. the delivery member cover has been maintained in the second position for e.g. a predetermined amount of time post administration completion, to ensure correct administration, based on for example the lapse of a certain time between the detection of the impact of the end click member and the second actuation.

Generally, all terms used in the claims are to be interpreted according to their ordinary meaning in the technical field, unless explicitly defined otherwise herein. All references to "a/an/the element, apparatus, component, means, etc. are to be interpreted openly as referring to at least one instance of the element, apparatus, component, means, etc., unless explicitly stated otherwise.

BRIEF DESCRIPTION OF THE FIGURES

The specific embodiments of the inventive concept will now be described, by way of example, with reference to the accompanying drawings, in which.

DETAILED DESCRIPTION

Figure 1:
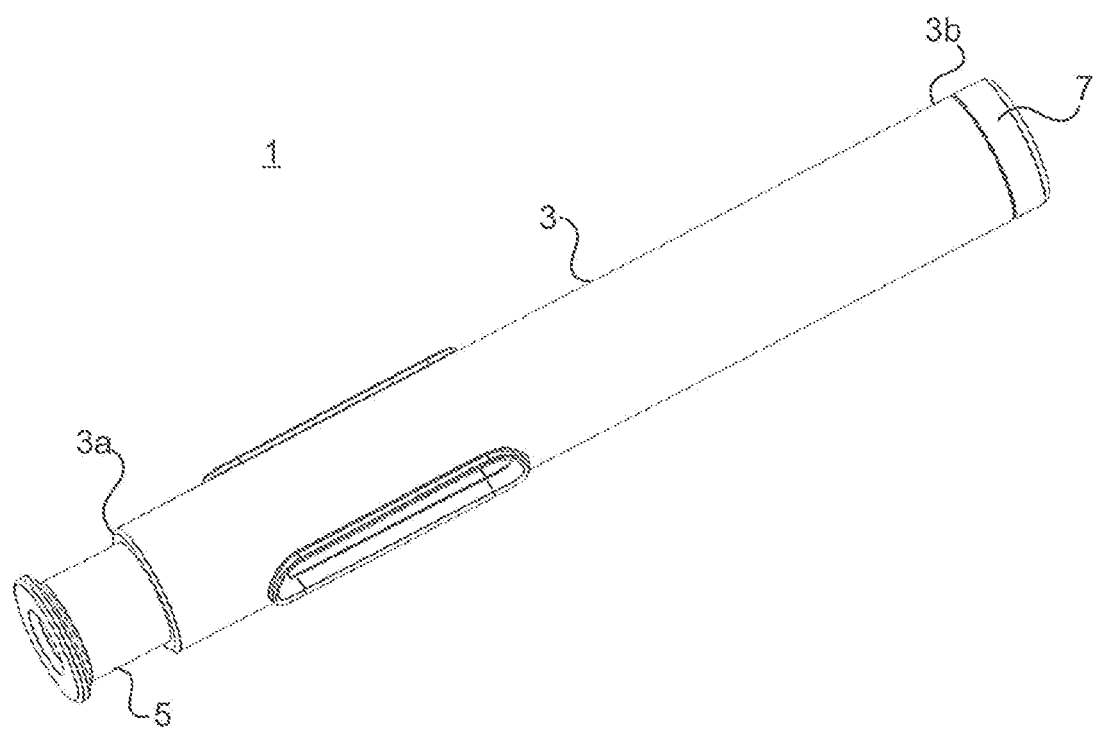
FIG. 1 is a perspective view of an example of a medicament delivery device.

The inventive concept will now be described more fully hereinafter with reference to the accompanying drawings, in which exemplifying embodiments are shown. The inventive concept may, however, be embodied in many different forms and should not be construed as limited to the embodiments set forth herein; rather, these embodiments are provided by way of example so that this disclosure will be thorough and complete, and will fully convey the scope of the inventive concept to those skilled in the art. Like numbers refer to like elements throughout the description.

With the term "proximal end" of an activation assembly is meant that end which is to be pointed towards the injection site during medicament injection. The same considerations also apply when referring to any component of the activation assembly. The "distal end" is the opposite end relative to the proximal end. With "proximal direction" and, equivalently, "proximally" is meant a direction from the distal end towards the proximal end, along the central axis of the activation assembly. With "distal direction" or "distally" is meant the opposite direction to "proximal direction".

The present disclosure relates to an activation assembly for a medicament delivery device. The medicament delivery device may for example an auto-injector or an eye dispenser.

The activation assembly comprises a proximally biased delivery member cover, a movable sleeve and a proximally biased activation sleeve. The delivery member cover has legs extending in the distal direction, and the delivery member cover is configured to receive the movable sleeve between the legs.

The delivery member cover is configured to be displaced axially relative to the movable sleeve, between a first position and a second position. The delivery member cover is configured to cooperate with the movable member so that when the delivery member cover is moved from the first position towards the second position, the linear movement of the delivery member cover causes movement of the movable sleeve, from a first movable sleeve position to a second movable sleeve position. In a typical example, the linear movement of the delivery member cover causes rotational movement of the movable sleeve, and the first movable sleeve position and the second movable sleeve position is a first rotational position and a second rotational position, respectively. The movable sleeve could according to one example also move a distance axially while being rotated by the linear movement of the delivery member cover.

The delivery member cover is furthermore configured to axially displace the activation sleeve when moved distally towards the second position. While being moved distally, the activation sleeve is configured to provide a first actuation of a sensor of an electronics assembly of a medicament delivery device. When the delivery member cover is returned from the second position to its initial position, i.e. the first position, the proximally biased activation sleeve will also move in the proximal direction, away from the sensor, to thereby provide a second actuation of the sensor.

The movable sleeve is furthermore configured to prevent movement of the delivery member cover from the first position towards the second position once the delivery member cover has returned from the second position to the first position.

An example of an activation assembly as well as of a medicament delivery device comprising the activation assembly will now be described with reference to FIGS. 1-9c.

FIG. 1 shows an example of a medicament delivery device. The particular example shows an auto-injector, but the medicament delivery device could alternatively be for example an eye dispenser.

The exemplified medicament delivery device 1 has a housing 3, having a proximal end 3a, and a distal end 3b, a delivery member cover 5 configured to be received by the housing 3, and an end cap 7. The delivery member cover 5 is configured to be axially displaced relative to the housing 3, between an extended position shown in FIG. 1, and a retracted position, in which the delivery member cover 5 is further received by the housing 3. The delivery member cover 5 is configured to be rotationally locked relative to the housing 3. The delivery member cover 5 is thus only able to move axially relative to the housing 3.

Figure 2:
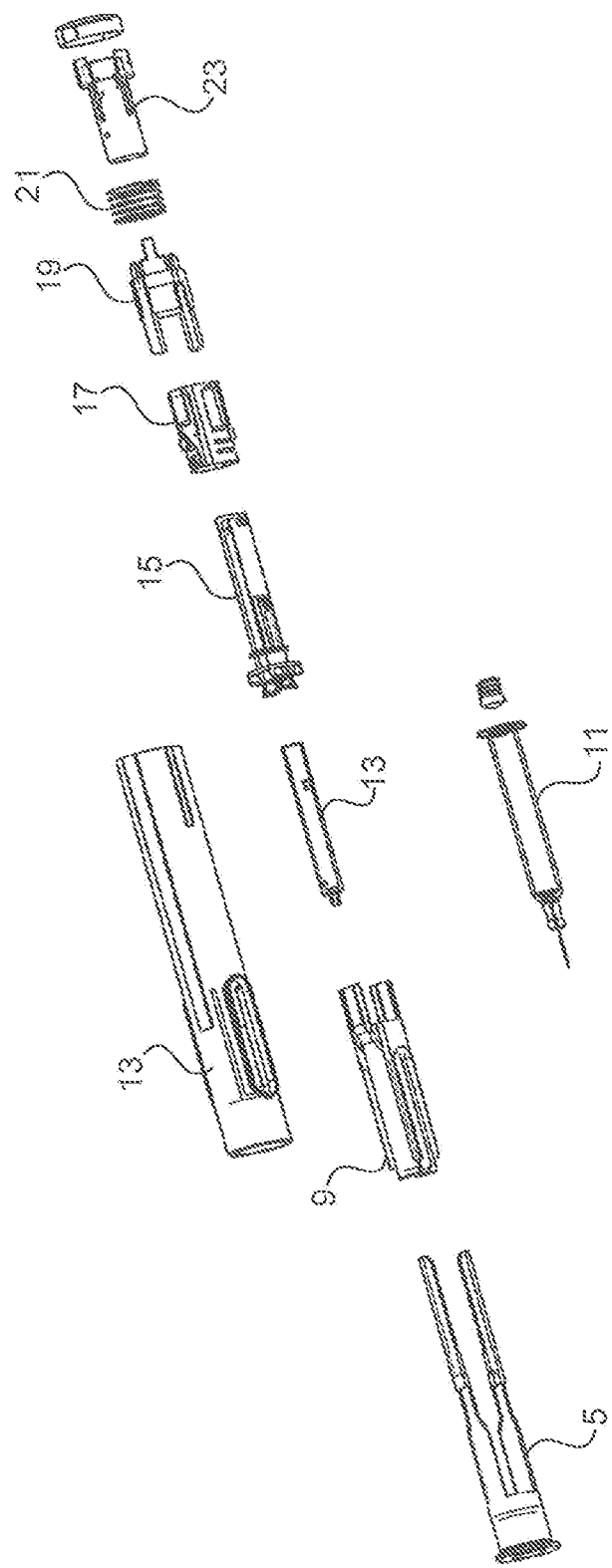
FIG. 2 is an exploded view of the medicament delivery device in FIG. 1.

FIG. 2 shows an exploded view of the medicament delivery device 1, showing a number of internal components thereof. Hereto, the medicament delivery device 1 further comprises a medicament container holder 9 configured to hold a medicament container 11, a plunger rod 13, a tubular extension member 15 configured to receive the plunger rod 13 in an axial opening, a movable sleeve 17, an activation sleeve 19, a resilient member 21, for example a spring, configured to bias the activation sleeve 19 in the proximal direction, and a tubular end member 23.

The medicament delivery device 1 may further comprise an electronics assembly, configured to be mounted for example under the end cap 7, i.e. proximally arranged relative to the end cap 7. Alternatively, the medicament delivery device 1 could be configured to be fitted with a supplementary device comprising the electronics assembly.

Figure 3:
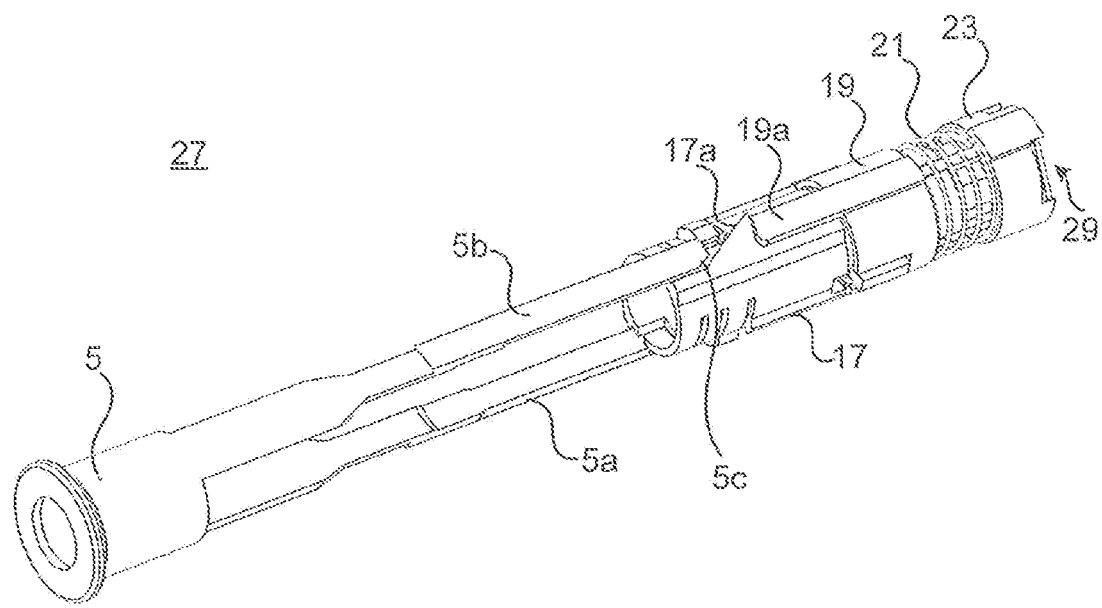
FIG. 3 is a perspective view of an example of an activation assembly, for use in the medicament delivery device in FIG. 1.

FIG. 3 shows a perspective view of an activation assembly 27 of the medicament delivery device 1, comprising the delivery member cover 5, the movable sleeve 17 and the activation sleeve 19. In the present example, the movable sleeve 17 is a rotator. The activation assembly 27 may also include an electronics assembly 29 arranged at a distal end portion of the activation assembly 27.

The delivery member cover 5, which has a tubular proximal end portion, has a first leg 5a and a second leg 5b extending in the distal direction. The movable sleeve 17 is configured to be received between the first leg 5a and the second leg 5b. The delivery member cover 5 has a distal end surfaces 5c, defining the respective end of the first leg 5a and the second leg 5b. The movable sleeve 17 has a radially extending portion 17a, forming a cam surface, configured to cooperate with a distal end surface 5c of a leg 5a, 5b. The movable sleeve 17 may have two such radially extending portions 17a, each configured to cooperate with a respective distal end surface 5c.

As previously mentioned, the delivery member cover 5 is configured to be moved axially between an extended position and a retracted position relative to the housing 3. The delivery member cover 5 is also configured to move axially relative to the movable sleeve 17, between a first position relative to the movable sleeve 17, corresponding to the extended position relative to the housing 3, and a second position relative to the movable sleeve 17, corresponding to the retracted position relative to the housing 3. In FIG. 3, the delivery member cover 5 is in the first position relative to the movable sleeve 17.

When the delivery member cover 5 is moved from the first position towards the second position relative to the movable sleeve 17, the distal end surface 5c cooperates with the radially extending portion 17a of the movable sleeve 17. Linear movement of the delivery member cover 5, from the first position towards the second position thereby causes movement of the movable sleeve 17, from a first movable sleeve position to a second movable sleeve position. In particular, the linear movement of the delivery member cover 5 causes rotation of the movable sleeve 17 as the distal end surface 5c slides along the radially extending portion 17a, the cam surface, of the movable sleeve 17 and the delivery member cover 5 is moved proximally. The movable sleeve 17 is then rotated from the first movable sleeve position, which according to the present example is a first rotational position, to the second movable sleeve position, which is a second rotational position.

The activation sleeve 19 has a main body provided with proximally extending legs 19a, of which one is visible in FIG. 3. The proximally extending legs 19a are configured to be aligned with a respective leg 5a and 5b of the delivery member cover 5. Initially, when the delivery member cover 5 is in the first position relative to the movable sleeve 17, and the movable sleeve is in the first rotational position, the radially extending portion 17a is located in between a leg 5a, 5b of the delivery member cover 5 and a proximally extending leg 19a of the activation sleeve 19, as shown in FIG. 3. When the delivery member cover 5 has been moved a certain distance towards the second position and the movable sleeve 17 has been rotated to a certain degree, the radially extending portion 17a will be rotated away from between the proximally extending leg 19a and leg 5a, and thus the delivery member cover 5 will be set in direct contact with the activation sleeve 19. Further distal movement of the delivery member cover 5 will thereby cause axial displacement of the activation sleeve 19, in the distal direction.

Figure 4:
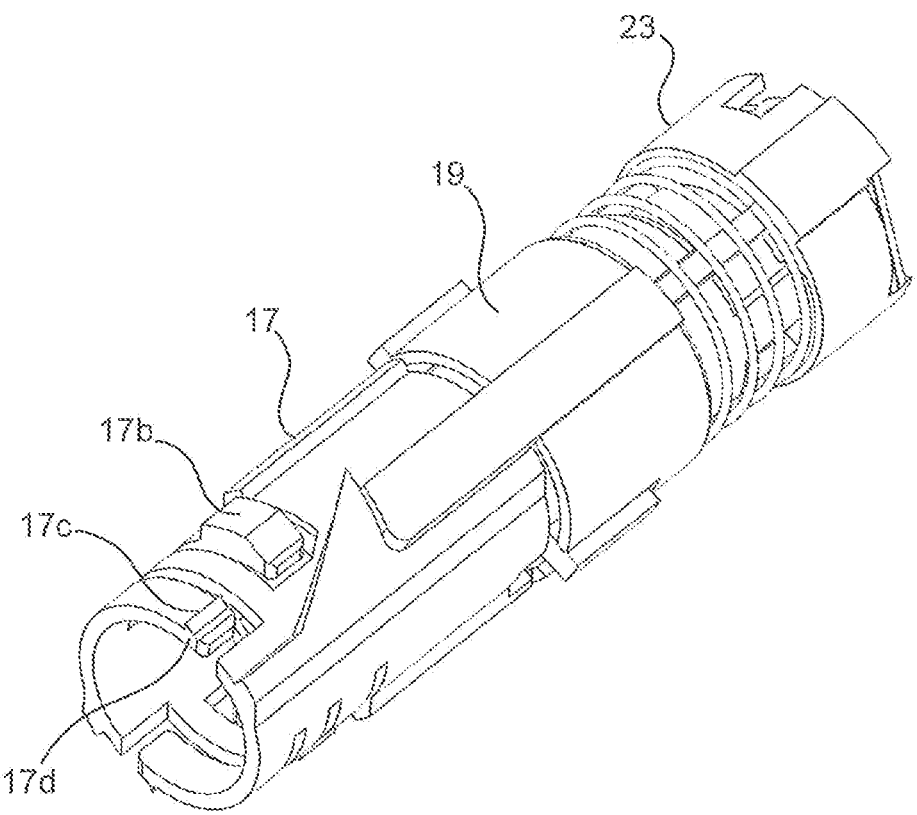
FIG. 4 is a perspective view of certain components of the activation assembly in FIG. 3.

Turning now to FIG. 4, the exemplified movable sleeve 17 has a tangentially extending radially flexible first tongue 17b configured to allow the delivery member cover 5 to move over the first tongue 17b from the first position towards the second position, when the movable sleeve 17 has not yet been fully rotated from the first rotational position to the second rotational position.

The first tongue 17b is furthermore configured to prevent the delivery member cover 5 to move from the first position to the second position when the movable sleeve 17 is in the second rotational position and the delivery member cover 5 has returned to the first position.

The first tongue 17b has an increasing thickness in the tangential direction in a tangential direction pointing away from the radially extending portion 17a. The first tongue 17 is thereby configured to enable the delivery member cover 5 to move over it, in the axial direction, when the delivery member cover 5 is moved from the first position towards the second position, and the movable sleeve 17 is being rotated towards the second rotational position.

According to the present example, the movable sleeve 17 has a radially outwards extending protrusion 17c configured to cooperate with the delivery member cover 5 to prevent rotation of the movable sleeve 17 from the second rotational position to the first rotational position. According to the present example, the movable sleeve 17 has a tangentially extending radially flexible second tongue 17d, and the radially outwards extending protrusion 17c is provided on the second tongue 17d.

As an alternative to the configuration with the second tongue 17d, the tubular end member 23, which is configured to be received by a distal portion of the movable member 17, may have an outer surface provided with an engagement structure configured to engage with the movable member 17 when the movable member 17 is set in the second rotational position.

The resilient member 21 may be configured to be arranged between the tubular end member 23 and a distal end of the activation sleeve 19, to thereby bias the activation sleeve 19 proximally.

Figure 5:
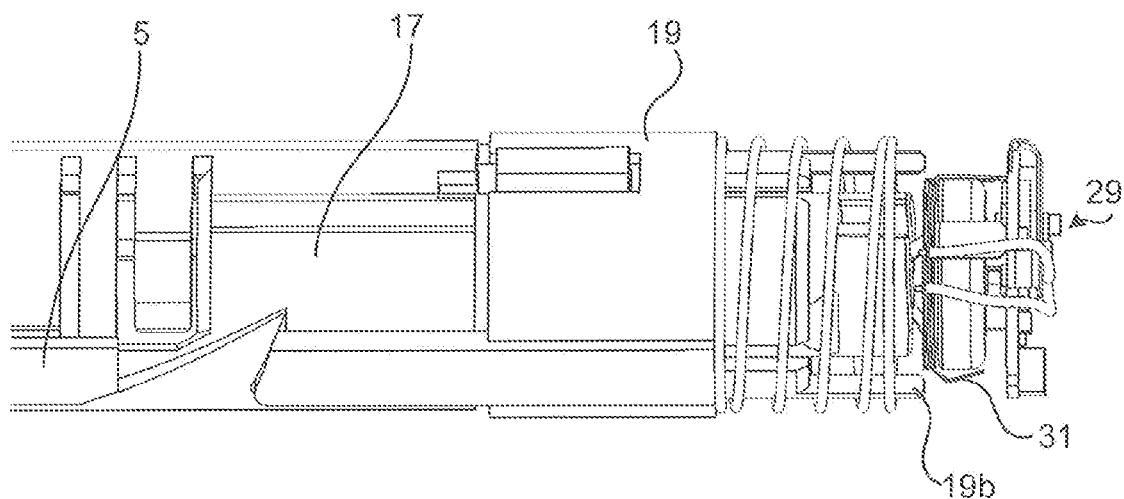
FIG. 5 shows a side view, with inter alia the housing removed, of a distal end of the medicament delivery device in FIG. 1.
Figure 6:
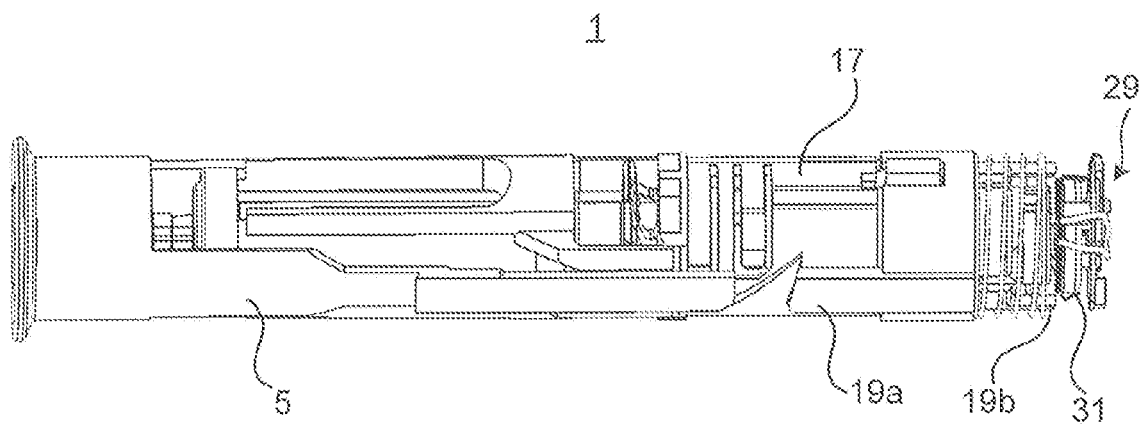
FIG. 6 is a side view, with the housing removed, of a first state of operation of the medicament delivery device.

FIG. 5 shows a distal end portion of the medicament delivery device 1, including an electronics assembly 29 arranged distally relative to the activation sleeve 19. The tubular end member 23 has been removed to expose the electronics assembly 29.

The electronics assembly 29 may comprise an energy storage unit, for example a battery, or in case the medicament delivery device 1 is capable of energy harvesting, a capacitor, processing circuitry configured to be powered by the energy storage unit, a storage medium comprising computer-executable components configured to be run on the processing circuitry, and a wireless transmitter configured to transmit data processed by the processing circuitry. The electronics assembly 29 furthermore comprises a sensor 31, for example a switch. According to the present example, the sensor 31 is a switch which has an elongated axial extension and which extends radially outwards, and which is radially flexible.

The activation sleeve 19 has a distally extending arm 19b configured to actuate the sensor 31. In FIG. 5 the delivery member cover 5 is in the first position and the movable sleeve 17 is in the first rotational position. Hereto, the activation sleeve 19 is in an initial position, in which it has not been moved in the distal direction. The sensor 31, i.e. the switch, is thus in this state of the medicament delivery device 1 not arranged in contact with the distally extending arm 19b. This state is better visible in FIG. 6 which shows the entire medicament delivery device 1, with the housing 3 removed.

With reference to FIGS. 7a-9c, the medicament administration procedure utilising medicament delivery device 1 will now be described. The delivery member cover 5 is in this procedure pressed towards the injection site, causing the delivery member cover 5 to move proximally into the housing 3, from the extended position to the retracted position, i.e. from the first position to the second position.

Figure 7A:
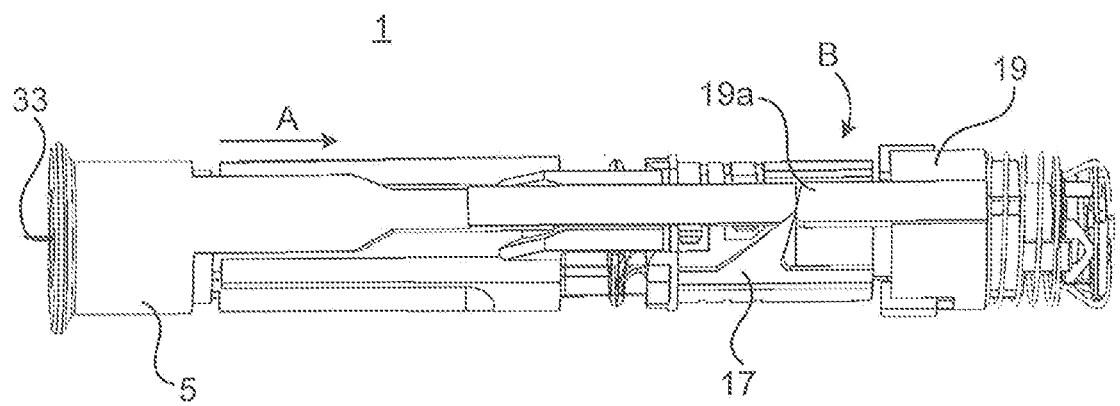
FIG. 7A shows the medicament delivery device, with the housing removed, when a delivery member cover has been moved distally to cooperate with an activation sleeve.

FIG. 7a shows a situation in which the delivery member cover 5 has been moved from the first position towards the second position relative to the movable sleeve 17, as shown by arrow A, to thereby expose the delivery member 33 which according to the present example is a needle. This causes a rotation of the movable sleeve 17, as shown by arrow B. The delivery member cover 5 has just been set in contact with the proximally extending leg 19a of the activation sleeve 19, and has moved the activation sleeve 19 slightly in the distal direction.

Figure 7B:
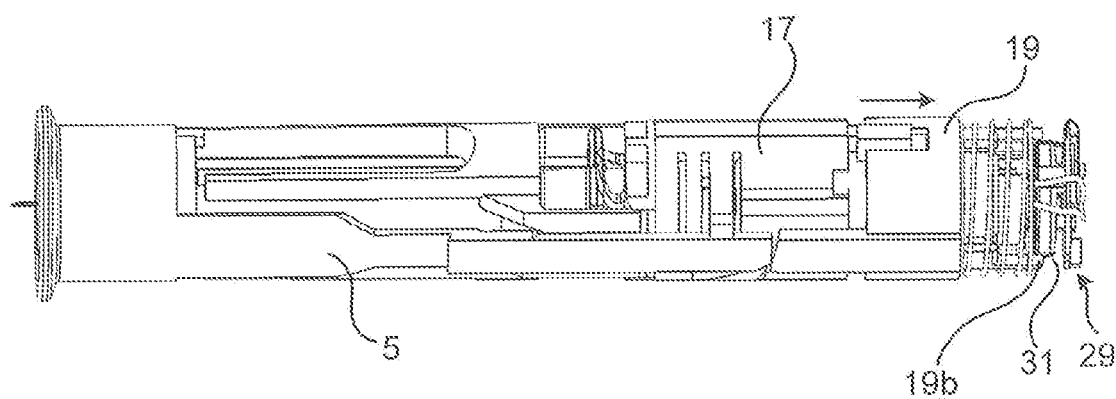
FIG. 7B shows the medicament delivery device, with the housing removed, when a delivery member cover has been moved distally to cooperate with an activation sleeve.

FIG. 7b shows a slight rotation of the entire medicament delivery device 1, to better visualise the effect of the distal movement of the activation sleeve 19.

Figure 8A:
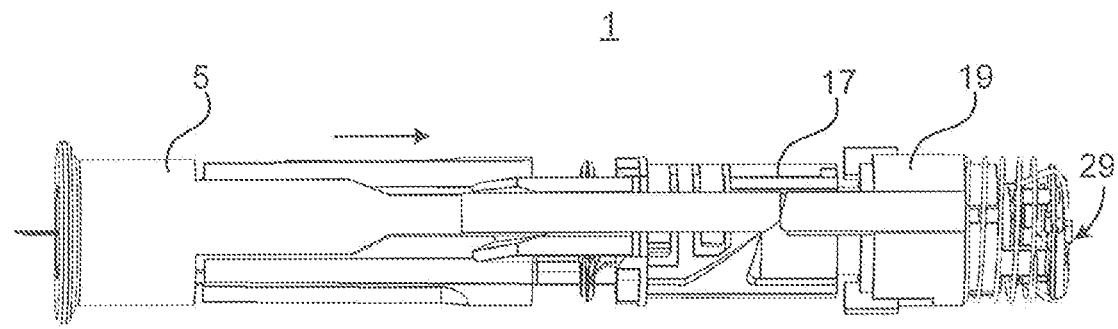
FIG. 8A shows the medicament delivery device, with the housing removed, when a delivery member cover has been moved fully distally.

FIG. 8a depicts a stage of the medicament administration procedure when the delivery member cover 5 has been moved even further in the distal direction, essentially to the second position relative to the movable sleeve 17. The movable sleeve 17 has thus been further rotated, and essentially obtained its second rotational position.

Figure 8B:
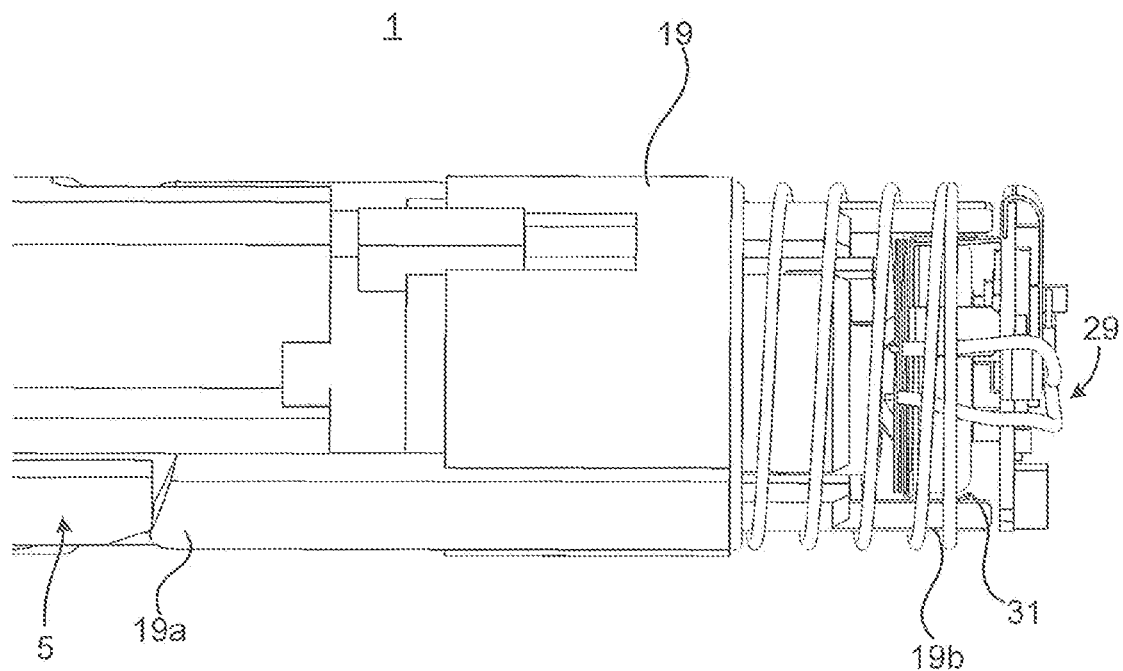
FIG. 8B shows the medicament delivery device, with the housing removed, when a delivery member cover has been moved fully distally.

FIG. 8b shows a close-up view of a distal end portion of the medicament delivery device 1 in the state shown in FIG. 8a, but with the medicament delivery device 1 having been slightly rotated. The distally extending arm 19b has moved past the switch 31 axially. The switch 31, which initially extended radially beyond the axial path of the distally extending arm 19b, has thus been pressed radially inwards by the distally extending arm 19b. The distally extending arm 19b hence contacts the switch 31, and presses it radially inwards. As long as the delivery member cover 5 is in the second position, or is pushed sufficiently in the distal direction, the switch 31 will maintain contact with the distally extending arm 19b and it will consequently be pressed radially inwards during this time. The activation sleeve 19 hence provides a first actuation of the switch 31.

The switch 31 may for example trigger the energy storage unit to power the processing circuitry, and/or it may cause the processing circuitry to register activation, the initiation of a medicament administration procedure, of the medicament delivery device 1.

The stroke, or stroke length, of the activation sleeve 19 is relatively long, while the stroke length of the switch is relatively short compared to the stroke length of the activation sleeve 19. Since the distally extending arm 19b is allowed to move axially past the switch 31 while actuating it, the mechanical tolerances between these cooperating members does not have to be that precise, which is highly advantageous in a manufacturing process.

Figure 9A:
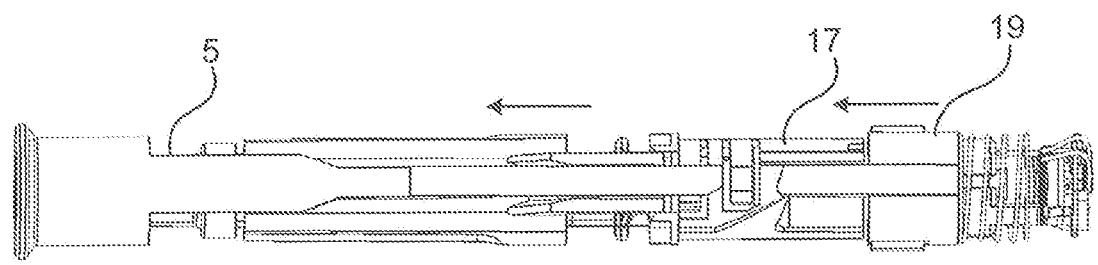
FIG. 9A shows the medicament delivery device, with the housing removed, when a delivery member cover has returned to its first position, its initial position.

FIG. 9a shows the medicament delivery device 1 when the proximally biased delivery member cover 5 has returned from the second position to the first position. It can be noted that the movable sleeve 17 remains in the second rotational position. Due to the proximal biasing of the activation sleeve 19, the activation sleeve 19 is returned to its initial position, concurrently with the proximal movement of the delivery member cover 5.

Figure 9B:
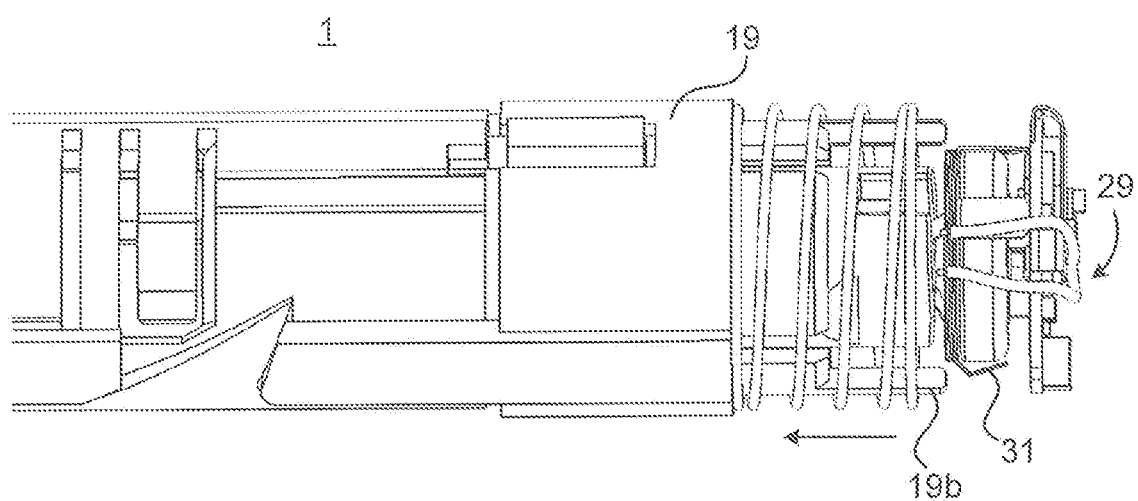
FIG. 9B shows the medicament delivery device, with the housing removed, when a delivery member cover has returned to its first position, its initial position.

FIG. 9b shows a close-up view of the distal end portion of the medicament delivery device 1, in the state shown in FIG. 9a but with the medicament delivery device 1 having been slightly rotated. As can be seen, the distally extending arm 19b has moved axially in the proximal direction, causing a release of contact with the switch 31. The activation sleeve 19 hence provides a second actuation of the switch 31, when the contact between the activation sleeve 19 and the switch 31 ceases. Since the delivery member cover 5 is moved back towards the first position when the medicament delivery device 1 is removed from the injection site, this second actuation also provides an indication that the medicament administration procedure is being finalised or completed.

The second actuation of the switch 31 may thus for example cause a registration of the completion of the medicament administration procedure by the electronics assembly 29. Additionally, the second actuation may for example also cause the processing circuitry to transmit the previously registered commencement of medicament administration procedure by means of the wireless transmitter and/or of the registration of completion of the medicament administration procedure. According to on example, the electronics assembly may be configured to shut down after a predetermined amount of time after the second actuation.

Figure 9C:
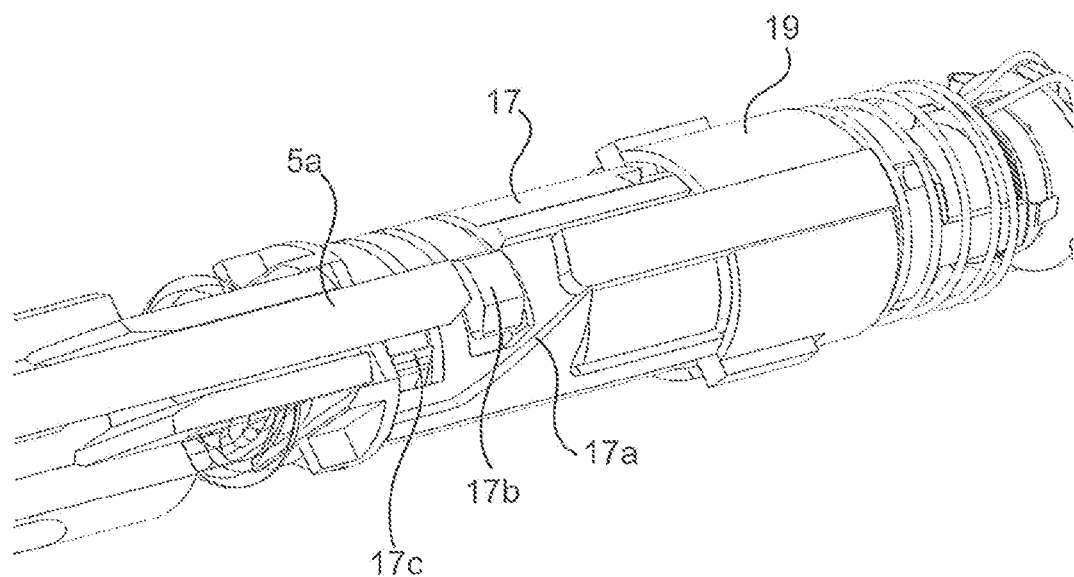
FIG. 9C shows an example of a blocking feature for preventing distal movement of the delivery member cover once returned to the initial position shown in FIGS. 9A-9B.

FIG. 9c shows the final state of the medicament delivery device 1, as shown in FIGS. 9a and 9b. Since the movable sleeve 17 has been rotated, and is in the second rotational position, the first tongue 17b is arranged in front of, i.e. axially aligned with and distally arranged from the first leg 5a of the delivery member cover 5. The delivery member cover 5 is thus prevented from being moved distally towards the second position once it has returned to the first position. Additionally, the radially outwards extending protrusion 17c is now arranged between the radially extending portion 17a and the first leg 5a of the delivery member cover 5, preventing the movable sleeve 17 from rotating back from the second rotational position to the first rotational position.

According to one example of the medicament delivery device 1, the tubular extension member 15 may be provided with radially flexible arms, and the medicament delivery device 1 may comprise a signal generating member, for example a U-shaped bracket provided with two longitudinally extending legs, configured to be received by the tubular extension member and the plunger rod 13 configured to be received between the legs of the U-shaped bracket. The movable sleeve 17 is configured to receive the tubular extension member 15, and the radially flexible arms are configured to be pressed radially inwards by the inner surface of the movable sleeve. The plunger rod 13, which has radial recesses configured to receive a respective one of the radially flexible arms therein, is thereby maintained in an initial axial position. The movable sleeve 17 may furthermore have an inner surface provided with recesses. When the movable sleeve 17 is being rotated, the radially flexible arms, which initially are pressed radially inwards by the inner surface of the movable sleeve, will be able to flex radially outwards, into the recesses of the movable sleeve 17. The plunger rod 13 is thereby released from its axially fixed position. The medicament delivery device 1 may also include a resilient member, for example a spring, configured to bias the U-shaped bracket in the distal direction, and a movable rod provided distally from and axially aligned with the U-shaped bracket. When the plunger rod 13 is released and moved in the proximal direction, the resilient member will cause the U-shaped bracket to be thrown backwards, i.e. in the distal direction towards the movable rod, which may be configured to actuate a sensor or switch different from the sensor 31. In this case, this audible click may be used as additional input concerning the stages of the medicament administration procedure. This audible click should appear prior to the second actuation of the switch 31, and it provides an indication that the medicament expulsion has been completed successfully. For this purpose, the electronics assembly may be configured to determine the time between the first actuation of the switch 31 and the detection of the audible click and/or the time between the detection of the audible click and the second actuation of the switch 31.

The inventive concept has mainly been described above with reference to a few examples. However, as is readily appreciated by a person skilled in the art, other embodiments than the ones disclosed above are equally possible within the scope of the inventive concept, as defined by the appended claims.

The invention claimed is:

1. An activation assembly for a medicament delivery device, wherein the activation assembly comprises:
   a delivery member cover comprising a distally extending leg having a first cam surface;
   a movable sleeve comprising a second cam surface slidably engaged with the first cam surface, where the movable sleeve rotates from an initial position to an activation position as the delivery member cover moves axially in a distal direction; and an activation sleeve that moves axially relative to the movable sleeve to activate the medicament delivery device, where the activation sleeve comprises a proximally directed leg that will engage the moveable sleeve when the moveable sleeve is in the initial position to prevent the axial movement of the activation sleeve relative to the delivery member cover and to prevent actuation of the activation assembly, wherein when the movable sleeve moves to the activation position from the initial position, the activation sleeve is no longer blocked from moving axially relative to the movable sleeve, wherein when the delivery member cover moves axially in the distal direction relative to the movable sleeve the first cam surface slidably engages the second cam surface causing the movable sleeve to rotate to the activation position thereby allowing actuation of the activation assembly.

2. The activation assembly of claim 1, wherein a proximal movement of the delivery member cover after the moveable sleeve has moved to the activation position causes the delivery member cover to axial lock axially in an extended position.

3. The activation assembly of claim 1, wherein the delivery member cover is biased in a proximal direction relative to the moveable sleeve.

4. The activation assembly of claim 1 further comprising a plunger rod positioned within the activation sleeve and configured to move axially from a start position to an end position.

5. The activation assembly of claim 4, wherein the plunger rod comprises a radial recess that is engaged with a flexible arm to hold the plunger rod in the start position.

6. The activation assembly of claim 5, wherein the flexible arm disengages from the recess after the movable sleeve rotates to the activation position.

7. The activation assembly of claim 5, wherein disengagement of the flexible arm from the recess causes the plunger rod to move axially in a proximal direction relative to the movable sleeve from the start position to the end position.

8. An activation assembly for a medicament delivery device, wherein the activation assembly comprises:
a delivery member cover comprising a distally extending leg having a cam surface;
a movable sleeve comprising a distal facing stop surface, where the movable sleeve and the stop surface rotate from an initial position to an activation position as the cam surface of the delivery member cover engages the movable sleeve and moves axially in a distal direction; and
an activation sleeve that moves axially relative to the movable sleeve to activate the medicament delivery device, where the activation sleeve comprises a proximally directed leg that will engage the stop surface when the moveable sleeve is in the initial position to prevent axial movement of the activation sleeve relative to the delivery member cover and to prevent actuation of the activation assembly, wherein when the movable sleeve moves to the activation position from the initial position, the activation sleeve is no longer blocked from moving axially relative to the movable sleeve, wherein when the delivery member cover moves axially in the distal direction relative to the movable sleeve the cam surface slidably engages the movable sleeve causing the movable sleeve to rotate to the activation position thereby allowing actuation of the activation assembly.

9. The activation assembly of claim 8, wherein a proximal movement of the delivery member cover after the moveable sleeve has moved to the activation position causes the delivery member cover to lock axially in an extended position.

10. The activation assembly of claim 8, wherein the delivery member cover is biased in a proximal direction relative to the moveable sleeve.

11. The activation assembly of claim 8 further comprising a plunger rod positioned within the activation sleeve and configured to move axially from a start position to an end position.

12. The activation assembly of claim 11, wherein the plunger rod comprises a radial recess that is engaged with a flexible arm to hold the plunger rod in the start position.

13. The activation assembly of claim 12, wherein the flexible arm disengages from the recess after the movable sleeve rotates to the activation position.

14. The activation assembly of claim 12, wherein disengagement of the flexible arm from the recess causes the plunger rod to move axially in a proximal direction relative to the movable sleeve from the start position to the end position.

15. A method of activating an auto-injector comprising:
providing an activation assembly comprising a delivery member cover, a movable sleeve, and an activation sleeve, where the activation assembly is contained within a housing of the auto-injector;
preventing actuation of the auto-injector by axial alignment of a distal facing stop surface on the moveable sleeve with a proximally directed leg of the actuation sleeve such that the activation sleeve is blocked from moving axially relative to the movable sleeve to activate the medicament delivery device;
placing a proximal end of the delivery member cover against an injection site and pushing the housing towards the injection site to cause the delivery member cover to retract inside of the housing and to move a distally extending leg of the delivery member cover having a first cam surface relative to the movable sleeve; and
slidably engaging the first cam surface with a second cam surface located on the movable sleeve, thereby rotating the movable sleeve from an initial position to an activation position,
wherein rotation of the movable sleeve moves the stop surface out of alignment with the proximally directed leg of the actuation sleeve such that the activation sleeve is no longer blocked from moving axially relative to the movable sleeve, thereby allowing the activation sleeve to move axially and activating the auto-injector.

16. The method of claim 15 further comprising moving the delivery member cover proximally relative to and after the moveable sleeve has moved to the activation position to cause the delivery member cover to axially lock in an extended position.

17. The method of claim 15 further comprising biasing the delivery member cover in a proximal direction relative to the moveable sleeve.

18. The method of claim 15, wherein the activation assembly further comprises a plunger rod positioned within the activation sleeve, having a radial recess and configured to move axially from a start position to an end position.

19. The method of claim 18 further comprising disengaging a flexible arm from the radial recess after rotating the movable sleeve to the activation position so that the plunger rod is moves axially from the start position.

20. The method of claim 19 further comprising disengaging the flexible arm after slidably engaging the first cam surface with the second cam surface to cause the plunger rod to move axially in a proximal direction relative to the movable sleeve from the start position to the end position.

* * * * *